United States Patent [19]

Storey et al.

[11] Patent Number: 5,668,288

[45] Date of Patent: Sep. 16, 1997

[54] POLYESTER IONOMERS FOR IMPLANT FABRICATION

[75] Inventors: Robson F. Storey, Hattiesburg, Miss.; Z. David Deng, Carmel, Ind.; Todd P. Glancy, Fairmount, Ind.; Dale R. Peterson, Carmel, Ind.

[73] Assignee: DePuy Orthopaedics, Inc., Warsaw, Ind.

[21] Appl. No.: 633,120

[22] Filed: Apr. 16, 1996

[51] Int. Cl.$^6$ .................................................. C07D 213/22
[52] U.S. Cl. ........................ 546/257; 544/333; 546/321
[58] Field of Search ................................ 546/257, 321; 544/333

[56] References Cited

U.S. PATENT DOCUMENTS

| | | | |
|---|---|---|---|
| 3,946,027 | 3/1976 | Bossert et al. | 546/257 |
| 4,243,775 | 1/1981 | Rosensaft et al. | 525/415 |
| 4,347,234 | 8/1982 | Wahlig et al. | 424/15 |
| 4,595,713 | 6/1986 | St. John | 523/105 |
| 4,645,503 | 2/1987 | Lin et al. | 623/16 |
| 4,757,128 | 7/1988 | Domb et al. | 528/271 |
| 4,843,112 | 6/1989 | Gerhart et al. | 523/114 |
| 4,888,176 | 12/1989 | Langer et al. | 424/426 |
| 4,902,508 | 2/1990 | Badylak et al. | 424/95 |
| 4,906,474 | 3/1990 | Langer et al. | 424/428 |
| 4,956,178 | 9/1990 | Badylak et al. | 424/551 |
| 5,019,379 | 5/1991 | Domb et al. | 424/78 |
| 5,085,861 | 2/1992 | Gerhart et al. | 424/78.17 |
| 5,133,755 | 7/1992 | Brekke | 623/16 |
| 5,171,579 | 12/1992 | Ron et al. | 424/486 |
| 5,206,341 | 4/1993 | Ibay et al. | 528/361 |
| 5,286,763 | 2/1994 | Gerhart et al. | 514/772.4 |
| 5,366,508 | 11/1994 | Brekke | 623/16 |
| 5,464,929 | 11/1995 | Bezwada et al. | 528/361 |

FOREIGN PATENT DOCUMENTS

| | | |
|---|---|---|
| 92111732.1 | 1/1993 | European Pat. Off. . |
| 3-45265 | 2/1991 | Japan . |

OTHER PUBLICATIONS

Ferguson, David et al., *Bovine Bone Morphogenetic (bBMP) Fraction–induced Repair of Craniotomy Defects in the Rhesus Monkey (Macaca speciosa)*, Clinical Orthopaedics and Related Research, No. 219, pp. 251–258, Jun. 1987.
Gerhart, T.N. et al., *Antibiotic Release From an Experimental Biodegradable Bone Cement*, Journal of Orthopaedic Research, 6:585–592, 1988.
Hollinger, Jeffrey, *Factors for Osseous Repair and Delivery: Part II*, Craniofac. Surg., 4 (3), pp. 135–141, (Jul. 1993).
Hollinger, Jeffrey O. et al., *Osseous Wound Healing with Xenogeneic Bone Implants with a Biodegradable Carrier*, Surgery, vol. 107, No. 1, pp. 50–54, Jan. 1990.
Hollinger, Jeffrey O. et al., *Biodegradable Bone Repair Materials*, Clinical Orthopaedics and Related Research, No. 207, pp. 290–305, (Jun., 1986).
Kamegai, Akihide et al., *Bone Formation Under the Influence of Bone Morphogenetic Protein/Self–Setting Apatite Cement Composite as a Delivery System*, Bio–Medical Materials and Engineering, vol. 4, No. 4, pp. 291–307, 1994.

Kenley, Richard A. et al., *Biotechnology and Bone Graft Substitutes*, Pharmaceutical Research, vol. 10, No. 10, pp. 1393–1401, 1993.
Kohn, Joachim et al., *Polymerization Reactions Involving the Side Chains of α–L–Amino Acids*, J. Am. Chem. Soc., 109 pp. 817–820, 1987.
Kulkarmi, R.K. et al., *Polylactic Acid for Surgical Implants*, Arch. Surg. vol. 93, pp. 839–843, Nov. 1966.
Kulkarni, R.K. et al., *Biodegradable Poly(lactic acid) Polymers*, J. Biomed. Mater. Res., vol. 5 pp. 169–181, 1971. 56–262, 1993.
Laurencin, C.T. et al., *Bioerodible Polyanhydrides for Antibiotic Drug Delivery: In Vivo Osteomyelitis Treatment in a Rat Model System*, Journal of Orthopaedic Research, vol. 11, No. 2, pp. 256–262, (1983).
Leong, K.W. et al., *Bioerodible Polyanhydrides as Drug–Carrier Matrices. I: Characterization, Degradation, and Release Characteristics*, J. Biomed. Mater. Res., vol. 19, pp. 941–955, 1985.
Lindholm, T.S. et al., *Functional Carriers for Bone Morphogenetic Proteins*, Annales Chirurgiae at Gynaecologiae, No. 82, pp. 3–12, 1993.
Lovell, T.P. et al., *Augmentation of Spinal Fusion with Bone Morphogenetic Protein in Dogs*, Clinical Orthopaedics and Related Research, No. 243, pp. 266–274, Jun., 1989.
Miki, Takashi et al., *Effect of Freeze–Dried Poly–L–Lactic Acid Discs Mixed with Bone Morphogenetic Protein on the Healing of Rat Skull Defects*, J. Oral. Maxillofac. Surg., No. 52, pp. 387–391, 1994.
Miyamoto, Shimpei et al., *Evaluation of Polylactic Acid Homopolymers as Carriers for Bone Morphogenetic Protein*, Clinical Orthopaedics and Related Research, No. 278, pp. 274–285, May, 1992.
Miyamoto, Shimpei et al., *Polylactic Acid–Polyethylene Glycol Block Copolymer*, Clinical Orthopaedics and Related Research, No. 294, pp. 333–343, Sep., 1993.
Miyamoto, S. et al., *Bone Induction and Bone Repair by Composites of Bone Morphogenetic Protein and Biodegradable Synthetic Polymers*, Annales Chirutgiae et Gynaecologiae, No. 82, pp. 69–76, 1993.
Rokkanen, Pentti U., *Absorable Materials in Orthopaedic Surgery*, Ann. Med., No. 23, pp. 109–115, 1991.
Sidman, K.R. et al., *Biodegradable, Implantable Sustained Release Systems Based on Glutamic Acid Copolymers*, Journal of Membrane Science, vol. 7, No. 3, pp. 277–291, 1980.
Storey, Robson F. et al., *New Epoxy–Terminated Oligoesters: Precursors to Totally Biodegradable Networks*, Journal of Polymer Science: Part A: Polymer Chemistry, vol. 31, pp. 1825–1838, 1993.
Storey, Robson F. et al., *Novel Synthesis of (Carboxylic Acid)–Telechelic Poly(ε–Caprolactone)*. Abstracts of Papers of the American Chemical Society, 1996, v.211, Mar. 24, p. 113.

Primary Examiner—Terressa Mosley
Attorney, Agent, or Firm—Barnes & Thornburg

[57] ABSTRACT

Carboxy-terminated polyester ionomers useful for bioresorbable implant construction are described. They comprise biocompatible salts or partial salts of mono- or bis-carboxyterminated polyesters.

20 Claims, No Drawings

POLYESTER IONOMERS FOR IMPLANT FABRICATION

FIELD OF INVENTION

This invention relates to bioerodable polymers for use in medical applications, for example, implants for controlled release of bioactive substances and tissue repair. More particularly, this invention is directed to biocompatible, non-toxic salts of mono- or bis-carboxy-terminated polyesters and their use in formulation of improved implant matrices.

BACKGROUND AND SUMMARY OF THE INVENTION

Many polymers have been used in biomedical applications, including polyesters, polyvinyl acetate, polyacrylates, polyorthoesters, and polyanhydrides. One of the advantages of polyesters in such applications is that they are both biodegradable and biocompatible.

Aliphatic polyesters have been widely used in the area of biomaterials for implantable drug delivery devices, sutures, and general tissue supports, after injury or surgery. The polyesters traditionally of greatest interest in the area of biomaterials are derived from lactide, glycolide, and ε-caprolactone monomers, with a fairly broad range of degradation profiles accessible through various termonomer combinations. The ester linkages in these aliphatic polyesters are hydrolytically and/or enzymatically labile and render the polymers degradable in aqueous environments. However, in many cases it is desirable to produce unique bioerosion profiles outside of the normal range available by in vivo hydrolytic ester cleavage and concomitant solubilization of polyester based implants. Often, more rapid initial degradation, or specific bioerosion/biodegradation profiles are desired. One way to achieve enhanced rates of bioerosion is to select polymers with higher intrinsic solubility/erodability in vivo. However, biodegradable polymers selected for enhanced rate of bioerosion typically have less desirable/structural/chemical characteristics for implant function. One approach to modify enhanced implant degradation profiles has been to substitute anhydride linkages for all or some portion of the ester linkages, along with hydrophobic modifications of the polymer chain to prevent bulk degradation.

In accordance with the present invention, polyester ionomers, salts of carboxy-terminated polyesters, are utilized for implant fabrication. The polyester ionomers exhibit the desired structural/functional characteristics of the polyester, however, with enhanced in vivo solubility, thereby facilitating the solubilization of polymer molecules from the surface of the implant in vivo. Subsequent hydrolysis of the solubilized polyester components in serum at sites removed from the point of implantation, helps to prevent the occurrence of localized pH gradients which can be detrimental to the surrounding tissue viability. Thus, the use of salts of biodegradable carboxy-terminated polyesters in bioerodable implant structures in accordance with the present invention allows fabrication of implants with the needed structural and functional properties, further with good serum solubility of the polyester component.

In accordance with the present invention, polyester ionomers, salts of carboxy-terminated polyesters, are prepared and used as biomaterials for fabrication of implantable constructs for drug delivery and tissue support and reconstruction. The polyester ionomers exhibit good solubility even at higher molecular weights dictated by implant structural/functional requirements. The polyesters are prepared from and degrade into naturally occurring metabolites for enhanced biocompatibility. The polyester ionomers are prepared from the corresponding carboxy-terminated polyesters by neutralization or partial neutralization with biocompatible, pharmaceutically acceptable salt-forming bases. In one aspect of the present invention there is provided compositions comprising biodegradable carboxy-terminated polyesters in combination with the corresponding ionomers. The physical properties of polyester ionomers can be controlled by degree of neutralization of the corresponding carboxy-terminated polyesters and to some extent by selection of the neutralizing base. The polyester ionomers can be used alone or in combination with their carboxy-terminated polyester precursor for use in construction of improved implant matrix compositions for tissue repair and/or prolonged release of biologically active compounds.

DETAILED DESCRIPTION OF THE INVENTION

There is provided in accordance with this invention, polyester ionomers, more particularly non-toxic salts of biodegradable carboxy-terminated polyester of the general formula RO~PE~COOH or HOOC~PE~COOH wherein R is hydrogen or $C_1$-$C_4$ alkyl and ~PE~ is a divalent residue of a polyester. The polyester can comprise a homopolymer, copolymer, or terpolymer of biocompatible hydroxy acids, for example, lactic acid, glycolic acid, ε-hydroxy caproic acid, and γ-hydroxy valeric acid. Alternatively, the polyester can be formed using copolymerization of a polyhydric alcohol and a biocompatible polycarboxylic acid. Most typically such copolymers are formed between dihydric alcohols, for example, propylene glycol for biocompatibility and biocompatible dicarboxylic acids. Representative carboxylic acids for formation of the polyesters useful for preparing the polyester ionomers in accordance with this invention include Kreb's cycle intermediates such as citric, isocitric, cis-akonitic, α-ketoglutaric, succinic, maleic, oxaloacetic and fumaric acid. Many of such carboxylic acids have additional functionalities which can enable further cross-linking of the polymers if desirable.

The polyesters can be further modified, for example, by reaction with a cyclic carboxylic anhydride to convert residual hydroxy functionality to the carboxy-terminated forms useful for preparation of the present polyester ionomers.

In one embodiment of the invention the carboxy-terminated polyesters utilized for preparation of the polyester ionomers are selected to have a threshold water solubility between about 0.01 and about 500 mg/ml of water, more preferably about 0.1 to about 500 mg/ml of water, most preferably about 0.5 to about 400 mg/ml of water at about 25° C. (ambient temperature). The polyester precursors have a weight average molecular of about 400 to about 10,000, more typically about 1000 to about 5000. Conversion of those compounds by neutralization with pharmaceutically acceptable bases produces the present ionomers having enhanced water solubility relative to the carboxy-terminated polyester precursors but retaining other polymer functionality. Conversion to the corresponding salt forms by stoichiometric or less than stoichiometric neutralization of the terminal carboxy functionalities provide a polyester ionomer or ionomer-containing composition that exhibits many of the structural and chemical properties of the carboxy-terminated precursor but with much enhanced water (and serum) solubility. The enhanced water solubility facilitates dissolution of the polyester in vivo. Subsequent hydrolysis of the solubilized polyester components in serum at a site removed from the point of implantation, for example, helps to minimize the occurrence of localized pH gradients at the implant site which can be detrimental to surrounding tissue viability. Such is particularly important when the implant constructs are used for tissue repair.

The polyester ionomers of this invention are prepared from mono- or bis-carboxy-terminated polyesters. Generally the carboxy-terminated polyester is dissolved in an organic solvent and neutralized by the addition of a physiologically acceptable base. In one embodiment of the present invention the neutralization is carried out with less than a stoichiometric amount of base to produce a composition comprising a carboxy-terminated polyester and its corresponding ionomer, the ratio of those components dependent on the degree of neutralization.

Suitable bases for use in forming the present polyester ionomers in accordance with this invention include hydroxides of Group Ia or Group IIa metals including preferably the hydroxides of lithium, sodium, potassium, magnesium and calcium and as well, physiologically compatible salt-forming amines.

Following neutralization of the carboxy-terminated polyester, the resulting ionomer can be isolated using standard isolation techniques. the ionomer is typically dried prior to use in fabrication of implant constructs.

The carboxy-terminated polyester starting materials for use in accordance with this invention can be prepared using art-recognized procedures for polyester synthesis. The carboxy-terminus (or termini) on such compounds can be formed by reaction of hydroxy functional polyesters with, for example, a stoichiometric amount of a cyclic anhydride of a $C_2$–$C_6$ dicarboxylic acid, such as succinic anhydride.

Bis-hydroxy functional polyesters are readily prepared by reaction of a dihydric alcohol initiator, for example, propylene glycol or ethylene glycol, with one or more cyclic hydroxy acid esters, for example lactide, glycolide or caprolactone. Reaction of such bis-hydroxy functional polyesters with cyclic anhydrides produces bis-carboxy functional polyesters useful for preparation of the present ionomers as described above.

The polyester prepolymers used for the preparation of the present ionomers can be prepared using art recognized polyester forming reaction chemistry, typically employing, for example, metal catalysts to promote ester-forming reactions. One problem with such prior art procedures is the difficulty in removing the metal catalyst from the product polyesters. Such is particularly crucial when the polyesters are intended for use in medical applications. It has been found that polyesters of hydroxy acids can be prepared in high yields and high purity with good control over structure/functionality by reacting the corresponding cyclic esters with a hydroxy functional initiator at elevated temperatures under substantially anhydrous conditions. Thus one preferred method for preparing a polyester compound for use in this invention consists essentially of reacting an initiator, for example a monohydric or dihydric alcohol with at least one cyclic hydroxy acid ester under substantially anhydrous conditions at elevated temperatures. The reaction is preferably carried out neat (an absence of solvent) at a temperature of about 100°–180° C., more preferably about 120°–160° C. The term "substantially anhydrous conditions" as utilized in defining the conditions for polyester formation requires simply that routine efforts be made to exclude water from the reaction mixture and can typically include such steps as pre-drying the reaction vessel with heat and carrying out the reaction under drying conditions.

The structure of the polyester is controlled by selection and stoichiometry of the cyclic hydroxy acid ester reactant (s) and the amount of initiator utilized with lower relative initiator amounts leading to higher average molecular weight product and higher relative amounts of initiator leading to lower average molecular weight product.

The hydroxy functional initiator can either be a monohydric alcohol, for example a $C_1$–$C_4$ alkanol, or a di-or polyhydric alcohol. Alternatively, the hydroxy functional initiator can be a hydroxy acid, for example glycolic acid. The product hydroxy-terminated polyesters can be readily converted to a carboxy-terminated polyester for use in preparation of the present polyester ionomers by reaction with a stoichiometric amount of a cyclic anhydride.

The method for preparing polyester polymers for use in preparing the present polyester ionomers this invention can be carried out as well in the presence of a cyclic carboxylic acid anhydride to provide directly the corresponding carboxy terminated polyester compound. The reaction is carried out under the same conditions as described above for preparing the polyester. Most typically the reaction is carried out using about equimolar amounts of a monohydric alcohol initiator and the cyclic anhydride. Where the initiator is a dihydric alcohol, the molar ratio of the cyclic anhydride to the initiator is preferably raised to about 2:1.

The polyester ionomers of the present invention are used in the preparation of bioresorbable implant constructs. Thus they can be used alone or with fillers for tissue support and reconstruction, or in combination with one or more biologically active agents to provide a source of prolonged release of such bioactive agent following implantation. The use and construction of such devices are well known in the art, and the present polyester ionomers can be substituted for prior art polymer compositions in art-recognized preparation of such devices.

Thus the implant constructs can be prepared by blending the polymer with one or more bioactive agents and optionally other excipients, for example, additives to optimize retention of biological activity and polymer functionality during sterilization, and sterilizing and packaging the implant formulation for surgical use. Sterilization can be accomplished by radiation with about 1 to about 3 mRad of gamma radiation or electron beam radiation. If the biologically active agent is a biologically active protein or peptide, biological activity can be optimized during sterilization by including in the formulation an extraneous protein, for example albumin or gelatin, and a free radical scavenger (antioxidant), for example propyl gallate, 3-t-butyl-4-hydroxyanisole (BHA) or ascorbic acid, in an amount effective to retard radiation induced degradation of the biologically active peptide. The sterilization is preferably conducted at low temperature, for example –70° C. When a filler is used in the composition with a biologically active peptide or protein, it is advantageous to form a mixture of the biologically active compound and an extraneous protein such as albumin or gelatin, and coat the filler with that formulation prior to blending the filler into the polyester ionomer.

The implant constructs can comprise about 1 to about 90%, more preferably about 30 to about 70 weight percent and most preferably about 35 to about 50 weight percent filler. The filler may be organic, inorganic or a combination of organic and inorganic fillers. Suitable fillers include bone chips, tricalcium phosphate, hydroxyapetite, powdered/dried small intestine submucosa (as describes in U.S. Pat. No. 4,902,508), bioglass granules, synthetic polymers, calcium carbonate, calcium sulfate, or collagen.

Examples of proteinaceous bioactive agents which can be included in the implant constructs include particularly growth factors such as fibroblast growth factor, a transforming growth factor (for example, TGF-$\beta_1$), a bone morphogenic protein, an epidermal growth factor, a platelet drive growth factor, or an insulin-like growth factor. Other bioactive agents which can be utilized alone or in combination with such growth factors are antibacterial agents, and in instances where the implant construct is to be used substantially as a matrix for prolonged release of a biologically active agent, any such active compound or composition currently utilized in treatment of disease in humans or animals can be included for release from the matrix.

EXAMPLE 1

Materials

The following reagents were used without further purification: chloroform-d (99.8 atom %, 1% TMS) (Aldrich), ε-caprolactone (Union Carbide), 1,2-dichloroethane (DCE) (Aldrich), diethylene glycol, 99% (DEG) (Aldrich), diphenylchlorophosphate, 99% (DPCP) (Aldrich), ethanol (EtOH), 100% (AAPER Alcohol and Chemical Co.), hexanes (Fisher), hydrochloric acid (HCL) (Fisher), magnesium sulfate (Fisher), methylene chloride (Fisher), 1-methylimidazole 99+% (NMIM) (Aldrich), sodium sulfate (Fisher), stannous 2-ethylhexanoate (stannous octate) (Sigma), succinic anhydride 97% (Aldrich), tetrahydrofuran (THF) (Fisher), and triethylamine, 99% (TEA) (Aldrich).

Hydroxyl-Terminated Polyesters

Polymerizations of ε-caprolactone (20–40 g) were carried out in the bulk under nitrogen using stannous octoate as catalyst at a concentration of $1.4 \times 10^{-4}$ mole per mole of monomer. Glassware was dried at 145°–155° C. for 24 h, fitted with rubber septa and cooled under a flow of dry nitrogen. Table I lists the initiator, monomer/initiator ratio, and reaction time and temperature for each polymerization. In Table I and throughout the description of this example, specific polymer samples are designated by two numbers separated by a hyphen; the first number (bold) indicates the generic type of polymer, and the second number is the sequential sample number. When reference is made to a generic type of polymer, only the bold, first number is used. Type 1 polymers are monohydric poly(ε-caprolactone)s initiated with ethanol; type 4 polymers are dihydric poly(ε-caprolactone)s initiated with diethylene glycol.

TABLE I

Initiator, monomer/initiator ratio, and reaction time and temperature for ε-caprolactone polymerizations

| Sample # | Initiator [I] | [M/I] | Temp | Reaction Time |
|---|---|---|---|---|
| 1-1 | EtOH | 8 | 65° C. | 5 h |
| | | | 115° C. | 15 h |
| 1-2 | EtOH | 10 | 65° C. | 5 h |
| | | | 115° C. | 15 h |
| 4-1 | DEG | 8 | 135° C. | 20 h |

A typical polymerization procedure was as follows: to a 250-mL boiling flask were added ε-caprolactone (32.43 g, $2.84 \times 10^{-1}$ mole), ethanol (3.29 g, $7.14 \times 10^{-2}$ mole), and stannous octoate (0.02 g). The flask was purged with nitrogen, sealed with a ground-glass stopper wrapped with Teflon® tape, and placed in an oil bath for 5 h at 65° C. followed by 15 h at 115° C. The polymerization was quenched by chilling the flask in an ice-water bath, and the polymer was dissolved in methylene chloride 25–35% (w/v), followed by precipitation into a ten-fold excess of stirred hexanes. The hexanes layer was decanted, and the polymer was washed with hexanes (3×100 mL). The isolated polymer was then redissolved, transferred to a specimen jar, dried for 24 h in an 80° C. oven, and then for 24–48 h at 80° C. in vacuo.

Carboxylic Acid-Terminated Polyesters

The hydroxyl end groups of poly(ε-caprolactone)s were converted to carboxylic acid end groups by reaction with succinic anhydride. Type 2 polymers were derived from ethanol-initiated, type 1 polymers and carry one carboxylic acid end group; type 5 polymers were derived from diethylene glycol-initiated, type 4 polymers and carry two carboxylic acid end groups. A typical procedure was as follows: to a 250-mL boiling flask equipped with a condenser, hot oil bath, magnetic stirrer, and nitrogen purge, were added ethanol-initiated poly(ε-caprolactone) (11.28 g, $2.26 \times 10^{-2}$ eq), succinic anhydride (3.39 g, $3.38 \times 10^{-2}$ mole), 1,2-dichloroethane (250 mL), and 1-methylimidazole (1.27 mL). The reaction mixture was heated for 15 h at 65°–70° C. After cooling, the solution was transferred to a separatory funnel and washed with 10% aqueous HCL (2×200 mL) and water (3×250 mL). The organic layer was dried over magnesium sulfate and filtered, and the solvent was removed under reduced pressure.

EXAMPLE 2

Materials

All reagents were used without further purification. Glycolic acid (99%), and succinic anhydride (97%) were purchased from the Aldrich Chemical Co. Stannous 2-ethylhexanoate (stannous octoate, 95%) was purchased from Sigma Chemical Co. ε-Caprolactone (high purity) was donated by Union Carbide Co.

Instrumentation

Gel permeation chromatography (GPC was used to determine molecular weights and molecular weight distributions, Mw/Mn, of polymer samples with respect to polystyrene standards (Polysciences Corporation).

$^{13}$C NMR spectra of the polymers were obtained on a Bruker AC-200 spectrometer using 5 mm o.d. tubes. Sample concentrations were about 25% (w/v) in CDCl3 containing 1% TMS as an internal reference.

Synthesis of α-Hydroxyl-ω-(Carboxylic Acid) Poly(ε-Caprolactone)

Glassware and stir bar were dried at 145°–155° C. for 24 h, fitted with rubber septa, and cooled under a flow of dry nitrogen. To a 40 mL test tube equipped with a 24/40 ground glass joint and magnetic stir bar were added glycolic acid ($5.1 \times 10^{-3}$ Mol, 0.39 g), ε-caprolactone ($8.8 \times 10^{-2}$ mol, 10 g) and stannous octoate catalyst ($1.4 \times 10^{-4}$ mol/mol monomer). The tube was purged with dry nitrogen gas, sealed with a glass stopper, and placed in a 140° C. constant temperature oil bath. The polymerization was carried out for 3.5 h with continuous stirring, and then quenched by immersing the tube in an icewater bath. The product was characterized by $^{13}$C NMR with no purification.

Synthesis of (Carboxylic Acid)-Telechelic Poly(ε-Caprolactone)

To a 40 mL test tube equipped with a 24/40 ground glass joint and magnetic stir bar were added glycolic acid ($5.4 \times 10^{-3}$ mol, 0.41 g), ε-caprolactone ($8.8 \times 10^{-2}$ mol, 10 g), succinic anhydride endcapper ($5.4 \times 10^{-3}$ mol, 0.55 g), and stannous octoate catalyst ($1.4 \times 10^{-4}$ mol/mol monomer). The tube was then purged with dry nitrogen gas, sealed, and placed in a 140° C. constant temperature oil bath. The polymerization was carried out for 12 h with continuous stirring, and then quenched by immersing the tube in an ice-water bath. The product was characterized by $^{13}$C NMR with no purification The synthesis of α-hydroxyl-ω-(carboxylic acid) poly(ε-caprolactone) involved the reaction of glycolic acid with ε-caprolactone in the presence of stannous octoate catalyst. In view of the reported role of hydroxyl groups as initiators of the ring-opening polymerization, this reaction was expected to produce an oligomer (A) containing a carboxylic acid group on one end, derived from a single, terminal unit of glycolic acid, and n units of ε-caprolactone, and terminating in a primary hydroxyl group at the other end of the chain. GPC chromatograms of aliquots taken at various times from the polymerization clearly show that conversion of the monomer was complete by 3.5 h. However, the final molecular weight (2700 g/mol) was higher than theoretical (2000 g/mol), which was attributed to the condensation polymerization of the α-hydroxyl-ω-(carboxylic acid) oligomers. Additional evidence for the occurrence of condensation polymerization was the appearance of water vapor on the walls of the flask during the quenching process.

(Carboxylic Acid)-Telechelic Poly(ε-Caprolactone)

The synthesis of (carboxylic acid)-telechelic poly(ε-caprolactone) involved ring-opening of ε-caprolactone initiated by glycolic acid, with termination by reaction with succinic anhydride. GPC was used to monitor the conversion of ε-caprolactone and the incorporation of succinic anhydride onto the polymer chain end. GPC chromatograms of aliquots taken at various times clearly show that by 12 h there is complete conversion of monomer and incorporation of succinic anhydride into the polymer.

EXAMPLE 3

(a) Synthesis of acid-terminated polymers

Glassware was dried at 145°–155° C. for 24 h, fitted with rubber septa, and cooled under a flow of dry nitrogen. Polymerizations were run in 250 mL Erlenmeyer flasks with 24/40 ground glass joints sealed with evacuated glass stoppers wrapped with teflon tape. To a flask (250 mL) containing a magnetic stir bar were added D,L-lactide (18.17 g, $1.26 \times 10^{-1}$ mol), glycolide (14.63 g, $1.26 \times 10^{-1}$ mol), ε-caprolactone (7.20 g, $6.30 \times 10^{-2}$ mol), glycolic acid (1.66 g, $2.18 \times 10^{-2}$ mol), succinic anhydride (2.19 g, $2.18 \times 10^{-2}$ mol). The flask was purged with nitrogen and heated in a 135° C. constant temperature bath for 20 h with continuous stirring. At 65 h of reaction, the temperature was lowered to 110° C. The polymerization was allowed to proceed for 146 h and was then quenched in an ice-water bath. The product was a ~2000 g/mole bis-carboxy-terminated PLGC terpolymer.

(b) Analytical titration procedure (2,000 g/mol sample)

To a 125 mL Erlenmeyer flask was added a (~2,000 g/mol) polymer sample (0.30 g–0.40 g). The polymer sample was completely dissolved in THF (50 mL) and water (15 mL) was added to the solution. Phenolphthalein (1 g/100 mL MeOH) (5 drops) was added to the polymer solution, and the flask was placed in an ice bath. The sample was titrated with an aqueous solution of NaOH (0.5047N) to a light pink end point. An average equivalent weight was calculated from the values of at least three titrations.

(c) Bulk polymer titration procedure (2,000 g/mol sample)

To a 1000 mL Erlenmeyer flask was added a (~2,000 g/mol) polymer sample (34.32 g), and the polymer was dissolved in THF (450 mL). The average equivalent weight from the above procedure was used to calculate the exact amount of titrant (85.3 mL, 0.5047N aqueous NaOH) necessary to completely neutralize the polymer sample. This amount was slowly added to the polymer solution as it was stirred in an ice bath. The product PLGC ionomer is dried in vacuo.

(d) Polyester Ionomer Preparation

Following the same general procedure as in (c) above ionomer compositions were prepared from a diethylene glycol initiated, succinic anhydride terminated PLGC terpolymer (~2000 g/mol).

| Wt. of PLGC | ml of NaOH (0.5022 N) | Wt. of Ca(OH)$_2$ | Ionomer Ion Content |
|---|---|---|---|
| (1) 3.9818 g | 7.37 | — | 85% Na$^+$; 15% H$^+$ |
| (2) 4.0312 g | 7.90 | — | 90% Na$^+$; 10% H$^+$ |
| (3) 4.1240 g | 8.53 | — | 95% Na$^+$; 5% H$^+$ |
| (4) 3.5219 g | 7.37 | .0143 g | 10% Ca$^{++}$; 90% Na$^+$ |
| (5) 3.8724 g | 7.90 | .0314 g | 20% Ca$^{++}$; 80% Na$^+$ |
| (6) 3.6620 g | 8.53 | .0445 g | 30% Ca$^{++}$; 70% Na$^+$ |

(e) Procedure for determination of polymer water solubility

1. Dissolve the polymer (50 mg) in tetrahydrofuran (THF) in a 25-mL glass test tube.
2. Evaporate the THF by air drying at room temperature, leaving a thin film of polymer coating the bottom of the test tube.
3. Add water (10 mL) to the test tube; mix the water and the polymer; allow the mixture to stand at room temperature for 24 hours.
4. Pipette the solution into a pre-weighed cup.
5. Evaporate the water under vacuum at 40° C.
6. Weigh the cup containing the polymer and calculate the amount of polymer in solution by subtracting the weight of the empty container.

EXAMPLE 4

Synthesis of poly(ε-caprolactone) in the absence of metal catalyst

Glassware and stir bar were dried 145°–155° C. for 24 h, fitted with rubber septa, and cooled under a flow of dry nitrogen. Polymerizations were run in 40 mL test tubes with 24/40 ground glass joints sealed with evacuated glass stopper wrapped with Teflon tape. To this test tube was added the appropriate amounts of ε-caprolactone monomer and glycolic acid initiator that would result in the desired molecular weight. The tube was purged with nitrogen and the glass was flamed to aid in the removal of residual water. The tube was then heated in a 135° C. constant temperature bath for the appropriate amount of time (2.5 h for 1000 g/mole).

EXAMPLE 5

Synthesis of acid terminated poly(ε-caprolactone) in the absence of metal catalyst Glassware and stir bar were dried at 145°–155° C. for 24 h, fitted with rubber septa, and cooled under a flow of dry nitrogen. Polymerizations were run in 40 mL test tubes with 24/40 ground glass joints sealed with evacuated glass stoppers wrapped with Teflon tape. to this test tube was added the appropriate amounts of ε-caprolactone monomer, glycolic acid initiator and succinic anhydride endcapper that would result in the desired molecular weight. the tube was purged with nitrogen and the glass was flamed to aid in the removal of residual water. The tube was then heated in a 135° C. constant temperature bath for the appropriate amount of time (generally 11 h).

EXAMPLE 6

Synthesis of acid terminated poly(D,L-lactide-co-glycolide-co-ε-caprolactone) in the absence of metal catalyst Glassware and stir bar were dried at 145°–155° C. for 24 h, fitted with rubber septa, and cooled under a flow of dry nitrogen. Polymerizations were run in 40 mL test tubes with 24/40 ground glass joints sealed with evacuated glass stoppers wrapped with Teflon tape. To this test tube was added the appropriate amounts of D,L-lactide, glycolide, and ε-caprolactone monomers, glycolic acid initiator and succinic anhydride endcapper that would result in the desired molecular weight. The tube was purged with nitrogen and the glass was flamed to aid in the removal of residual water. The tube was then heated in a 135° C. constant temperature bath for 102 h, at which time the temperature was reduced to 130° C. for 37.5 h which was then further reduced in temperature to 100° C. for 50 hours. Maximum D,L-lactide incorporation was reached at 189.5 hours.

EXAMPLE 7

Preparation of Polyester Ionomer Implant Construct

Reagents

Tricalcium phosphate: DePuy, 149 μ to 250 μ diameter

TGF-$\beta_1$: Genentech, 0.73 mg/mL

PLGC Polymer: Poly(lactide: glycolide: ε-caprolactone) (40:40:20) Na$^+$ ionomer (MW 2,000)(Example 3(c))

Coating Buffer: 20 mM Na acetate, pH 5.0 (Sigma cat #S-5889)

Gelatin Buffer: 2.5% Gelatin (250 mg/10 mL water), 100 Bloom General Foods

Rinse Buffer: PBS pH 7.4, Boehringer Mannheim cat. 100-961

Antioxidant: 0.2% N-propyl gallate in water (20 mg/10 mL; heat in microwave to place in solution) Sigma cat P-3130

Procedure

1. Add the desired amount of TGF-$\beta_1$ to the coating buffer (2 mL/g of TCP).
2. Mix the TGF-$\beta_1$ coating buffer solution with dry TCP in a siliconized polypropylene container.
3. Incubate the mixture at room temperature 3 hours with constant, gentle mixing.
4. Let the TCP settle or gently centrifuge; separate the TGF-$\beta_1$ coating buffer by decanting.
5. Add rinse buffer (same volume as coating buffer), mix and separate it by decanting.
6. Repeat rinse step.
7. Add antioxidant solution (same volume as the rinse buffer); mix and separate it by decanting.
8. Add gelatin buffer to the TGF-$\beta_1$-coated TCP (1.25 mL buffer/g TCP).
9. Add TCP/buffer mixture to the viscous PLGC polymer and mix [0.796 g (44%) of polymer/1 g (56%) of TCP].
10. Quickly freeze the matrix with liquid N$_2$
11. Lyophilize the matrix.

The matrix should be stored dry at −70° C. It will readily adsorb water from the atmosphere. The matrix can be sterilized by gamma radiation (2.5 Mrads) in a N$_2$ atmosphere in a sealed foil pack.

EXAMPLE 8

Dissolution and Release of Polyester Blends

This example demonstrates how the use of polyester ionomers can be used to adjust degradation and delivery of a biological substance in a desired time frame.

(a) Dissolution Rate

Method: TCP (50 mg) was mixed with enough polymer to bind all the TCP. The mixture was dried completely in a vacuum oven. The dry mix was weighed and placed in phosphate buffered saline (5 mL). The weight of the matrix that remained bound together was measured daily. Incubation during this process was at room temp. Complete dissolution was defined as the point at which no matrix material remained bound together.

Table II summarizes the results of tests made with random PLGC terpolymers in a ratio of 40%L-40%G-20%C with different end groups. Each terpolymer had a molecular weight of 2,000. The ionomer samples were prepared by carboxylating PLGC and then neutralizing the carboxylated material with NaOH. (See Example 3.)

TABLE II

DISSOLUTION STUDIES WITH PLGC TERPOLYMERS*

| Polymer End Group | Days to Complete Dissolution |
|---|---|
| OH | 50+ |
| $COO^-$ 50% $Na^+$ | 30 |
| $COO^-$ 100% $Na^+$ | 4 |

*PLGC ratio 40:40:20

(b) Release Rate

The release of TGF-$\beta_1$ from a PLGC/TCP/TGF-$\beta_1$ matrix, prepared as described in Example 7, was measured. The TGF-$\beta_1$ was extracted and assayed by ELISA as follows:

Undiluted horse serum (Sigma Cat #H-1270) and 0.02% by weight sodium azide were added to the sample. The amount of serum used depended upon the TGF-$\beta_1$ concentration; approximately 0.4 to 1 μg TGF-$\beta_1$/mL final concentration was targeted. The serum and TCP were incubated for a minimum of 12 hours (overnight) at room temperature with mixing. To remove TCP fines, the material was spun in a microfuge at 500×g for one minute.

The samples were then assayed by an ELISA assay to determine biological activity. The TGF-$\beta_1$ Capture ELISA protocol was as follows:

Material

1. Solid support: Dynatech Immulon II, cat#011-010-3450
2. Coating buffer: 0.05M Carbonate buffer pH 9.5 $Na_2CO_2$ (5.3 g/L)
3. Capture Mab: Mab<TGF-$\beta_1$>12H5, Genentech, lot #8268-61
4. Wash buffer: PBS, 0.05% Tween 20
5. Detection Mab: Mab<TGF-$\beta_1$>4All-HRP Genentech, lot 16904-30
6. Standard: TGF-$\beta_1$,Genentech, used same lot as unknown samples
7. Substrate: 3,3',5,5'-tetramethylbenzidine (TMB), Kirkegaard & Perry Catalog #50-76-100
8. Stop solution 1M $H_2SO_4$ Procedure:

A 96-well microtiter plate was coated with 0.5 μg/mL of Mab 12H5 in coating buffer and held at a temperature of 4° C. overnight at 100 μL/well. The plate was washed with wash buffer for 6 cycles in a Titertek Microplate washer 120, and the last volume of wash buffer was left in the wells. The 96-well plate was incubated for 10 minutes with the wash buffer and then emptied of the wash buffer. The TGF-$\beta_1$ samples were added to the washed plate and serially diluted in PBS at 100 µL/well. The TGF-$\beta_1$ samples were then incubated for 1 hour at room temperature. The plates were again washed with wash buffer for 6 cycles. 4All-HRP conjugate was then added to the plate and diluted to approximately 1:2000 in wash buffer, 100 µL/well. The plate was then incubated for 1 hour at room temperature. The plates were washed with wash buffer for 6 cycles. Next, 100 µL/well of substrate was added to the plate. The color was allowed to develop for 5 minutes. Then 50 µL/well of stop solution was added. The wavelength was read at 450 nm on a Molecular Devices Vmax.

The O.D. values were curve fit using a log linear regression. Standards of diluted TGF-$\beta_1$ were used to prepare the calibration curve. The multiple needed to superimpose the regression curve on the calibration curve at an O.D. value in the linear region was used to calculate the unknown concentration.

The results of the tests for release of TGF-$\beta_1$ from the PLGC/TCP/TGF-$\beta_1$ matrix are summarized in Table III:

TABLE III

RECOVERY OF TGF-$\beta_1$ FROM POLYMER MATRIX*

| Day | % Recovery of TGF-$\beta_1$ |
|---|---|
| 1 | 42% |
| 2 | 5.8% |
| 3 | 1% |
| 4 | <1% |
| 5 | <1% |
| 6 | <1% |

*PLGC (2:2:1), Na ionomer, MW 2,000-44%; TCP-56%; 2 mL TGF-$\beta_1$/g TCP.

The PLGC/TCP/TGF-$\beta_1$ matrix studied in this example had a high dissolution rate (as shown in part (a), Table 6, PLGC COO$^-$ Na$^+$ 100%) and also a fast release rate of TGF-$\beta_1$, i.e., the percent recovered dropped rapidly and the matrix continued to slowly release a low dose of TGF-$\beta_1$.

EXAMPLE 9

Formulation of Ionomer/Submucosa Matrix

Reagents

TGF-$\beta_1$: Genentech 0.73 mg/mL

PLGC Polymer: Poly(lactide: glycolide: ε-caprolactone) (40:40:20) Na ionomer; MW 2,000

Coating Buffer: 20 mM Na acetate, pH 5.0, (Sigma); 1% gelatin final concentration during coating (100 Bloom General Foods)

Antioxidant: 0.2% N-propyl gallate in water

Small Intestinal Submucosa (SIS): (Prepared in accordance with U.S. Pat. Nos. 4,902,508 and 4,956,178, supra, comminuted and lyophilized)

Procedure

1. Mix the desired amount of TGF-$\beta_1$ with coating buffer and SIS (1 mL buffer/100 mg SIS) to form a putty.
2. Incubate the mixture for 1 hour at room temperature.
3. Add antioxidant solution to the polymer and stir briefly at room temperature until a viscous solution is produced (4 mL of 0.02% by weight of antioxidant/g of polymer).
4. Mix the SIS/TGF-$\beta_1$ mixture with the viscous polymer solution.
5. Place the matrix in a container that: (a) can be frozen in liquid N$_2$ and (b) is shaped so the material can be coated evenly by the polymer, i.e., a glass petri dish.
6. Quickly freeze the matrix with liquid N$_2$.
7. Lyophilize the matrix.
8. Sterilize the polymer/matrix formulation as described in Example 7.

The polyester ionomer matrix prepared by this procedure had a final composition of 67% polyester ionomer, 33% SIS and contained 5 µg/mL TGF-$\beta_1$.

EXAMPLE 10

Polyester Solubility

The solubility of various polyesters was measured by dissolving the polyester in ultrapure water at room temperature. The results of these studies are summarized in Table IV.

TABLE IV

SOLUBILITY OF POLYESTERS

| Polymer | Ratio | (MW) | Solubility (g/L) |
|---|---|---|---|
| PL | — | 200 | 0.01 |
| PLG | 1:1 | 1000 | 1.4 |
| PLGC - OH | 2:2:1 | 2000 | 0.2 |
| PLGC - COOH | 2:2:1 | 2000 | 0.3 |
| PLGC - COONa | 2:2:1 | 2000 | 250 |

Some investigators have reported aseptic necrosis, inflammation, or sinus tracts in animals where poly($\alpha$-hydroxycarboxylic acid) implants have been used. It is generally thought that these adverse reactions were caused by local acidosis from the degradation of the polymer. Use of these new more soluble ionomer forms of the poly($\alpha$-hydroxycarboxylic acid) polymers avoids the danger of developing local acidosis at implant sites because the polymers dissolve and are diluted or carried away before quantities of acidic degradation products are produced.

EXAMPLE 11

Repair of Rabbit Radius with Polymer-Matrix Implant

A putty-like delivery matrix including a biologically active component (TGF-$\beta_1$) (See Example 7) was evaluated in vivo in the rabbit radius model.

EXPERIMENTAL DESIGN

Route of Administration

A test article, or the autogenous control, is implanted in the midshaft radial defect.

Overview

A 1.5-cm segment of the right radius is removed, producing a unilateral radial defect. The radial defect is implanted with a test material or a control article, or receives no implant, according to group assignment. The incision is closed, and the rabbits are allowed to survive for 8 weeks. At 8 weeks both radii are harvested.

Experimental Procedure

Xylazine/ketamine cocktail is used as the anesthetic agent. The cocktail is made by mixing xylazine (1.42 mL; 100 mg/mL) in ketamine (10 mL; 100 mg/mL). The rabbits are dosed initially at approximately 0.65 mL/kg I.M. (maximum of 3 mL per rabbit). An ear vein is catheterized, and additional anesthesia is given through this catheter at approximately 0.125 of the initial dose, as needed. The right radius is clipped free of hair, then shaved or depilatated and aseptically prepared for surgery.

Surgery

An incision is made mid-shaft over the anterior-medial surface of the right forearm. Soft tissue is reflected to expose the radius. The interosseous ligament between the radius and the ulna is separated, and the periosteum is excised from the radius for approximately 1.7 cm along the mid-shaft. A sterile spatula is placed between the radius and the ulna, and a 1.5 cm segment of the radius is removed, using a saw blade attached to a sagittal saw. The site is liberally irrigated with physiological saline during the ostectomy to prevent overheating of the bone margins.

Experimental Sequence

Each radial defect is filled with one of the test materials or the autogenous graft or is left empty. After the material is molded into position, the soft tissue is reapposed with absorbable suture and the skin is closed with non-absorbable suture.

The amount of material actually implanted is determined by weighing the formulation after preparation, before implanting (using a sterile foil weighing boat or a similar device), and then weighing the material not implanted.

The surgical site is radiographed to document the anatomic placement of the material, and the rabbits are returned to their cages. Buprenorphine hydrochloride (0.15 mg SQ) is administered daily for the first 3 days of recovery for pain.

The rabbits are maintained post surgery for 8 weeks and then terminated with Beuthanasia-D® Special Solution administered intravenously. The right and left radii are removed, and soft tissue is dissected free from these bones. The operated radius is examined histologically for the presence of bone within the defect site (indicating a union) and the presence of cartilage, soft tissue or cracks within the defect site (indicating a possible unstable union or nonunion). The results are scored histologically according to the scale: 0=failed, 1=poor, 2=moderate, 3=good, and 4=excellent.

The results of a study made using this procedure are summarized in Table V.

TABLE V

RABBIT RADIUS STUDY WITH PLGC IONOMER/TGF-$\beta_1$ MATRIX

| Treatment | Average Score | Std. Dev. | n[b] |
|---|---|---|---|
| Autograft (+ control) | 3.4 | 0.5 | 20 |
| Empty (− control) | 0.8 | 1.4 | 20 |
| Polymer[a]/TCP | 0 | 0 | 10 |
| Polymer[a]/TCP/TGF-$\beta_1$ ($\gamma$-sterilized) | 3.8 | 0.3 | 10 |

[a]PLGC COONa (2:2:1; MW 2,000)
[b]n = number of animals

This test demonstrated that constructs formed from the polyester ionomers of this invention can be used to repair long bones like the radius, which contain marrow, have a rich blood supply, and experience mechanical loading.

What is claimed:

1. A non-toxic salt of a biodegradable carboxy-terminated polyester of the general formula RO~PE~COOH or HOOC~PE~COOH wherein R is hydrogen or $C_1$–$C_4$ alkyl and ~PE~ is a divalent residue of a polyester comprising a homopolymer, copolymer or terpolymer of biocompatible hydroxy acids or a copolymer of biocompatible dihydric alcohols and biocompatible dicarboxylic acids.

2. The salt of claim 1 wherein the polyester has a weight average molecular weight range of about 400 to about 10,000.

3. The salt of claim 1 wherein the carboxy-terminated polyester has a water solubility of about 0.01 to about 500 mg/ml.

4. The salt of claim 1 wherein the carboxy-terminated polyester is of the formula RO~PE~COOH.

5. The salt of claim 1 wherein the carboxy-terminated polyester is of the formula HOOC~PE~COOH.

6. The salt of claim 4 or claim 5 wherein the polyester comprises a homopolymer, copolymer or terpolymer of a biocompatible hydroxy acid.

7. The salt of claim 4 or claim 5 wherein the polyester comprises a copolymer of a biocompatible dihydric alcohol and a biocompatible dicarboxylic acid.

8. The salt of claim 4 or claim 5 wherein the polyester has a weight average molecular weight range of about 1000 to about 5000.

9. A composition of matter comprising a biodegradable carboxy-terminated polyester of the general formula RO~PE~COOH and a non-toxic salt thereof wherein R is hydrogen or $C_1$–$C_4$ alkyl and ~PE~ is a divalent residue of a polyester comprising a homopolymer, copolymer or terpolymer of biocompatible hydroxy acids or a copolymer of biocompatible dihydric alcohols and biocompatible dicarboxylic acids.

10. A composition of matter comprising a biodegradable, carboxy-terminated polyester of the general formula HOOC~PE~COOH and a non-toxic salt thereof wherein ~PE~ is a divalent residue of a polyester comprising a homopolymer, copolymer or terpolymer of biocompatible hydroxy acids or a copolymer of biocompatible dihydric alcohols and biocompatible dicarboxylic acids.

11. An improved matrix composition for tissue repair, said matrix composition comprising a bioerodable synthetic polymer and optionally a filler and/or a biologically active compound, wherein synthetic polymer comprises a non-toxic polyester salt of a biodegradable carboxy-terminated polyester of the general formula RO~PE~COOH or HOOC~PE~COOH wherein R is hydrogen or $C_1$–$C_4$ alkyl and ~PE~ is a divalent residue of a polyester comprising a homopolymer, copolymer or terpolymer of biocompatible hydroxy acids or a copolymer of biocompatible di- or trihydric alcohols and biocompatible dicarboxylic acids.

12. The improved implant matrix composition of claim 11 wherein the polyester has a weight average molecular weight range of about 400 to about 10,000.

13. The improved implant matrix composition of claim 11 wherein the polyester has a water solubility of about 0.01 to about 400 mg/ml.

14. The improved implant matrix composition of claim 11 wherein the polyester is of the formula RO~PE~COOH.

15. The improved implant matrix composition of claim 11 wherein the polyester is of the formula HOOC~PE~COOH.

16. The improved implant matrix composition of claim 11 wherein the polyester comprises a homopolymer, copolymer or terpolymer of a biocompatible hydroxy acid.

17. The improved implant matrix composition of claim 11 wherein the polyester comprises a copolymer of a biocompatible dihydric alcohol and a biocompatible dicarboxylic acid.

18. The improved implant matrix composition of claim 11 wherein the polyester has a weight average molecular weight range of about 1000 to about 5000.

19. The improved implant matrix of claim 11 wherein the synthetic polymer comprises a biodegradable carboxy-terminated polyester of the general formula RO~PE~COOH and a non-toxic, salt thereof wherein R is hydrogen or $C_1$–$C_4$ alkyl and ~PE~ is a divalent residue of a polyester comprising a homopolymer, copolymer or terpolymer of biocompatible hydroxy acids or a copolymer of biocompatible dihydric alcohols and biocompatible dicarboxylic acids.

20. The improved implant matrix of claim 11 wherein the synthetic polymer comprises a biodegradable carboxy-terminated polyester of the general formula HOOC~PE~COOH and a non-toxic salt thereof wherein ~PE~ is a divalent residue of a polyester comprising a homopolymer, copolymer or terpolymer of biocompatible hydroxy acids or a copolymer of biocompatible dihydric alcohols and biocompatible dicarboxylic acids.

* * * * *